(12) United States Patent
Niazi

(10) Patent No.: US 8,183,035 B1
(45) Date of Patent: May 22, 2012

(54) SINGLE CONTAINER MANUFACTURING OF BIOLOGICAL PRODUCT

(75) Inventor: Sarfaraz Niazi, Deerfield, IL (US)

(73) Assignee: Therapeutic Proteins International, LLC, Chicago, IL (US)

( * ) Notice: Subject to any disclaimer, the term of this patent is extended or adjusted under 35 U.S.C. 154(b) by 0 days.

(21) Appl. No.: 13/227,324

(22) Filed: Sep. 7, 2011

(51) Int. Cl.
*C12M 1/12* (2006.01)

(52) U.S. Cl. .................... 435/297.3; 435/296.1

(58) Field of Classification Search .......... 435/296.1, 435/297.3, 297.2, 297.1, 69.6; 47/1.4
See application file for complete search history.

(56) References Cited

U.S. PATENT DOCUMENTS

| | | | |
|---|---|---|---|
| 5,081,036 A | | 1/1992 | Familletti |
| 5,747,331 A | * | 5/1998 | Hartikainen et al. ......... 435/266 |
| 6,432,698 B1 | | 8/2002 | Gaugler |
| 6,723,555 B2 | | 4/2004 | Downs |
| 7,507,318 B2 | | 3/2009 | Lin |
| 7,629,167 B2 | * | 12/2009 | Hodge et al. ............... 435/289.1 |
| 7,699,976 B2 | | 4/2010 | Hansen |
| 7,875,448 B2 | * | 1/2011 | Furey ........................ 435/289.1 |
| 2006/0019391 A1 | * | 1/2006 | Marx et al. .................. 435/401 |
| 2008/0305539 A1 | * | 12/2008 | Hickey et al. ............. 435/289.1 |
| 2010/0311146 A1 | * | 12/2010 | Auton ........................ 435/252.8 |
| 2011/0198286 A1 | * | 8/2011 | Niazi ............................ 210/638 |

FOREIGN PATENT DOCUMENTS

JP 61-202680 * 9/1986

* cited by examiner

Primary Examiner — Ralph Gitomer
(74) Attorney, Agent, or Firm — Sarfaraz K. Niazi

(57) ABSTRACT

A method of manufacturing biological products in a single container from the growth of cells to purification of the product is performed in a flexible disposable bioreactor that uses only a compressed gas for mixing and gasification. A porous septum is used to create the gasification and mixing as well as to separate a chromatography media used to harvest and purify a biological product in the same container. The closed container can be used in any environment without the risk of contamination to the product or the risk of contamination of environment with the product. This allows large manufacturing of hazardous substances, drugs and vaccines anywhere at the lowest cost possible. Numerous applications can be found in counter-terrorism and biodefense operations as well in managing epidemic illnesses.

4 Claims, 2 Drawing Sheets

SINGLE CONTAINER MANUFACTURING OF BIOLOGICAL PRODUCT

BACKGROUND OF THE INVENTION

Bioreactors, which are typically chambers in which a cell culture is grown, have been produced in many forms. Frequently, bioreactors are used to grow a mammalian cell culture in which the cells produce an extracellular component, such as an antibody or recombinant protein. Bioreactors are also used for virus production. A separation process is performed in order to concentrate and purify the desired component from the bioreactor, which may, for example, be useful as a therapeutic or diagnostic agent. Bioreactors are complex mechanical devices that provide mainly the mixing and gasification of liquids to grow a biological culture; this step is followed by several additional unit processes including the separation of cells, filtration to reduce the volume of nutrient medium, loading onto chromatography columns and several steps of purification. In recent years, there has been a raised awareness to produce many biological products on a short turn around time, particularly as it relates to the products needed to combat terrorism-related needs; this also includes the need to quickly develop and manufacture vaccines and antibodies. Current methods require availability of clean rooms, large capital investment and lengthy and tedious processes to manufacture these products. There is a great unmet need for creating a bioreactor system that will be capable of producing biological products under the most optimal conditions, be able to combine all steps of biological product manufacturing within the same container and be of the lowest cost to own and operate. Additionally, this will be a closed system that can be installed and used anywhere without the need for clean rooms and where the operators will be protected by the product as well. Such an invention will change the course of drug discovery and manufacturing, making it possible to provide life-saving new drugs to mankind at an affordable cost. Independently, the invention will serve many critical needs of counter-terrorism operations as well as epidemic control.

Mixing and gasification are the main functions that every available bioreactor performs today. Generally, separate mechanical devices are provided to perform these functions but in some instances, bubble reactors are used where the mass of air moving upwards provides the mixing function as well. It is impossible to ideally combine the two functions in one—using gasification to mix fluids because of the imbalance between the gasification requirements and the mixing functionality. Many of the reactions in a bioreactor need to be performed in an environment that will protect the product from the environment and the personnel from the product; this requires establishment of clean room facilities that can cost millions of dollars to construct and validate. Additionally, many steps required in the purification of biological drugs are performed independently of the phase when the biological product is produced such as from CHO cells that secrete the product or bacteria that produce it as inclusion bodies.

A system that combines all steps in the manufacturing of biological products, from growing cells to secrete them to separating the biological product and purifying it within the same container that remains closed during the entire operation will change the way biological drugs are developed and manufactured. This will be most suitable for situations where a product needs to be manufactured quickly such as in counter-terrorism operations as well as when protecting the public from epidemics since this system will allow a quick deployment of the manufacturing. The ability to manufacture biological drugs in an uncontrolled environment will make it possible to manufacture a variety of products at a fraction of their current cost, increase their availability and the protection provided by the enclosed systems will permit manufacture of biological products that could not otherwise be done safely.

The aspect about combining the harvesting and purification of drugs within the bioreactor is novel and a disruptive technology. While the bioreactors are exclusively used for the purpose of growing bacteria or other cells, their role can be expanded to include other processes that can be completed within the bioreactor. There is an unmet need to develop a bioreactor for expressing and separating a biological product from other components in the nutrient medium, combining the steps of expressing and separating within the bioreactor by binding the biological product with a chromatography media within a bioreactor, discarding the nutrient medium and eluting the biological product as a concentrated solution; this will eliminate at least three steps in the separation and purification of biological products—filtration or centrifugation to remove cell culture, perform ultrafiltration for volume reduction, and purification of biological product by selective elution from the bioreactor; the last use makes the bioreactor a chromatography column.

The time and cost-consuming steps of filtration, chromatography and purification slow down the manufacturing process and add substantial capital cost requirement to establish cGMP-grade manufacturing operations, particularly in a clean room environment.

BRIEF SUMMARY OF THE INVENTION

The invention provides in one aspect a method for preparing a variety of biological products. The method comprises providing a bioreactor is suitable for housing a predetermined volume of nutrient medium and comprises: (a) a container having at least one interior wall; (b) a septum positioned within the container and defining a lower chamber and an upper chamber; (c) the septum having a plurality of pores that provides fluid communication between the lower chamber and the upper chamber; (d) at least one nutrient medium inlet; (c) at least one nutrient medium outlet; (d) at least one gas inlet; (e) at least one gas outlet. The bioreactor is operated by (f) adding a nutrient medium and a (g) biological culture, (h) adjusting the temperature of nutrient medium (i) starting a flow of gas to agitate the nutrient medium and absorb gas into nutrient medium and operating the bioreactor for sufficient length of time to allow the biological culture to produce the desired biological product. While the process can be stopped at this point, it can be continued by (j) adding a chromatography media in the bioreactor to bind the secreted biological product and then (k) subjecting it to several washing and purification steps to obtain a pure form of a biological product by using only one enclosed container.

The above method of preparing a biological product is performed inside a sealed container, preferably a two-dimensional flexible bag, that will allow these operations to be conducted in less controlled environment. Further, this allows the operators to be protected from the biological product in case this has any deleterious effects on humans.

DETAILED DESCRIPTION OF THE INVENTION

In one aspect, the present invention provides a bioreactor suitable for preparing a purified biological product from a predetermined volume of nutrient medium, and a related method of use.

Figure 1:
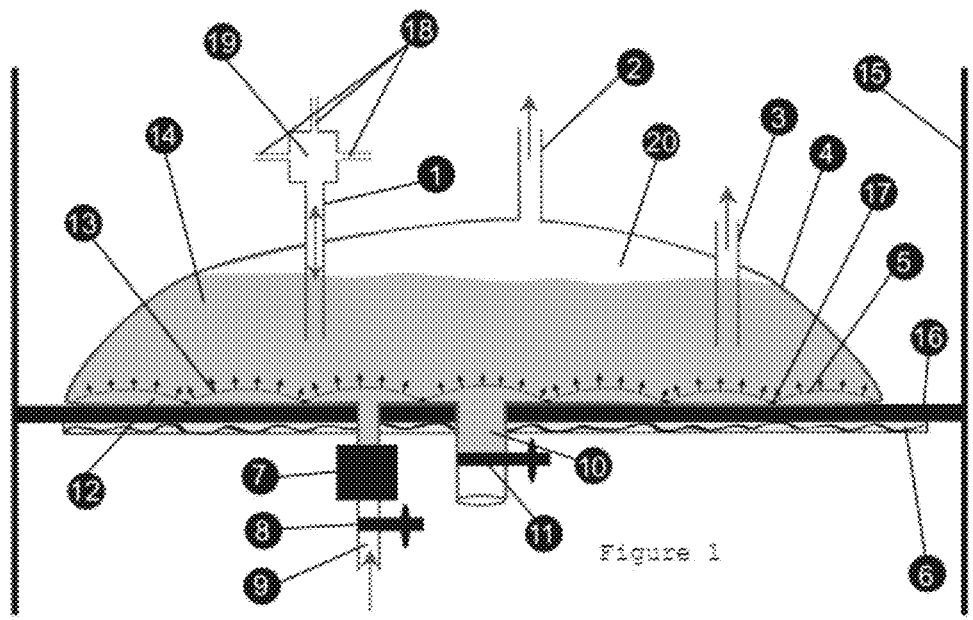
FIG. 1 is a side sectional view of a bioreactor in accordance with a preferred embodiment of the invention.

Turning initially to FIG. 1, a side sectional view of a preferred embodiment of the inventive bioreactor is illustrated. In this embodiment, there is provided a container 4 having at least one interior wall and, optionally, a support 16 for the container 4 affixed on a vertical structure 15.

The container 4 provides a receptacle in which the nutrient medium resides, and in which growth of the desired biological product occurs. The container has septum 13 positioned within the container and defining a lower chamber 12 and an upper chamber 20, the septum having a plurality of pores 5 that provides fluid communication between the lower chamber and the upper chamber. Additionally, the septum 13 is tufted 17 to the bottom of the container to prevent it from bloating during pressurization. The container 4 comprises several ports including a gas inlet 9, which further comprises a sterilizing filter 7 and a valve 8. The gas inlet 7 is connected to a source of compressed gas. Once the gas source is turned on, gas enters the lower chamber 12 through the gas inlet 9 after passing through the sterilizing filter 7. Since the plurality of the pores 5 in the septum 13 have smaller diameter, the flow of gas across the septum 13 is impeded, resulting in a build-up of pressure inside the lower chamber 12. Once a critical pressure is reached in the lower chamber, the gas breaks through the plurality of pores 5 and into the upper chamber 20 and travels through the contents of the container 4, finally breaking the surface of the liquid 14 in the container and finally exiting the container through a gas outlet 2.

The container also includes a valve 10 that controls removal of the nutrient medium and biological culture through liquid outlet 11. The upper chamber 20 further comprises a liquid inlet 1 to introduce nutrient medium and biological culture to the container 4 and having a manifold 19 that allows connections 18 to buffers, nutrient medium, biological culture and chromatography media; optionally a sampling port 3 is provided to remove the nutrient medium periodically for analysis of its contents.

Returning to FIG. 1, it is desirable that the container 4, particularly a flexible container as further described herein, be supported by a support, the latter preferably comprising platform 16 and side walls 15. The platform and side walls may be comprised of any suitable material, e.g., metal or rigid polymers, so long as it is sufficiently rigid to support the flexible container. Desirably, and as illustrated in FIG. 1, the platform (and the container) is raised relative to the floor or other surface. This permits inlets and outlets to be located on the side or the container which rests on the platform. For example, and as illustrated in this embodiment, it is desirable that the at least one gas inlet 9 of the container 4 be located on a portion of the container which is coextensive with the platform, wherein the platform includes an opening therethrough which permits the gas to pass through the platform and into the container 4 through the gas inlet 9. The container 4 rests on a support surface 16, which is in turn supported by a vertical structure 15, if needed. The lower surface of the support surface 16 additionally includes a means of heating of cooling 6 for the container 4.

The gas inlet 9 has an additional control valve 8 that is placed between the container 4 and the sterilizing filter 7; the control valve 8 is between the source of compressed gas and the sterilizing filter 7.

The hard support platform 16 additionally contains a heating element 6 attached to the side opposite to that that is in contact with container 4 to allow the nutrient medium to be kept at a desired temperature, most likely at 37° C.

Figure 2:
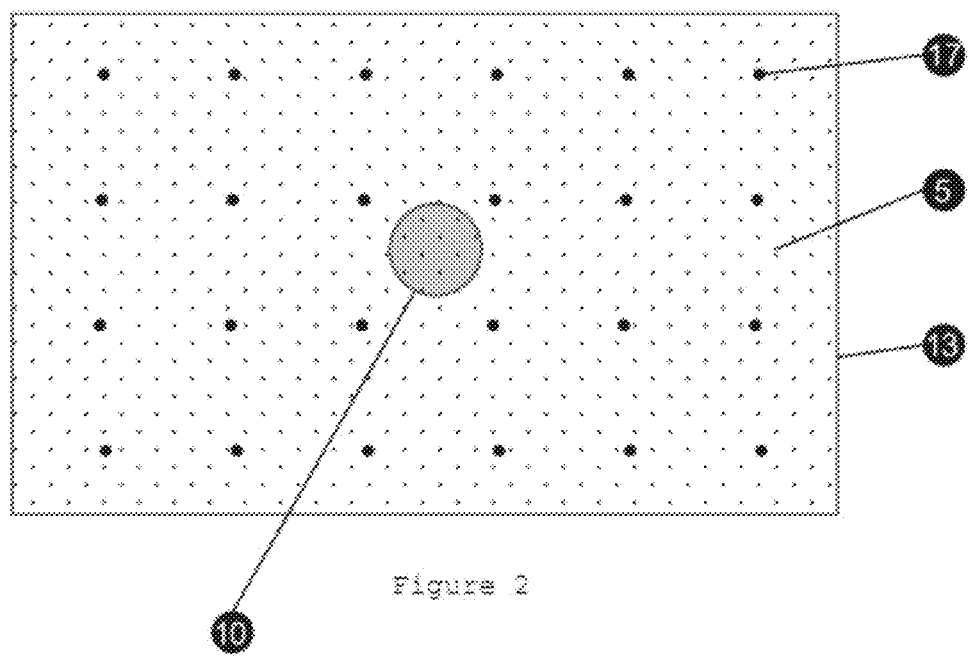
FIG. 2 is a topical view of the septum in a bioreactor in accordance with a preferred embodiment of the invention.

FIG. 2 shows a topical view of the septum 13, wherein the plurality of holes 5 is distributed evenly or in specific patterns throughout the horizontal surface of the septum 13. More specifically, the septum 13 comprises a flexible sheet of plastic of approximately the same size as the bottom dimension of the container 4 and that it has been perforated by mechanical means such using a laser beam, to create pores proportionally placed throughout the surface. The septum is sandwiched between the top and the bottom layer of the flexible bag and attached to the bottom surface in a tufted form 17 to keep the two layers from separating during pressurization. The pressure in the lower chamber forces the gas out of the pores 5 as fine bubbles inside the nutrient medium; it is understood that the nutrient medium will be present in both chambers of the container 4.

A method for producing and purifying a biological product using the present invention would comprise providing a bioreactor suitable for housing a predetermined volume of a nutrient medium comprising: a single-use flexible container having at least one interior wall and an inner volume; a septum positioned within the container and defining a lower chamber and an upper chamber, the septum having a plurality of pores ranging in size from 1 μm to 1000 μm, that provides fluid communication between the lower chamber and the upper chamber; at least one liquid inlet in the upper chamber with a dip tube reaching to the bottom of the upper chamber and in fluid communication with at least one source of a buffer solution, at least one source of a nutrient medium and at least one source of a biological culture; at least one liquid outlet in the lower chamber with a valve to control the rate of flow; at least one gas inlet in fluid communication with a source of compressed gas and located in the lower chamber further comprising a sterilizing filter positioned between the source of compressed gas and the container; at least one gas outlet in the upper chamber with means of controlling the rate of flow of gas; a means of heating or cooling the nutrient medium.

The bioreactor described above is operated in the present invention by introducing the nutrient medium into the container through the liquid inlet in the upper chamber; introducing a biological culture capable of growing in the nutrient medium and secreting a biological product in the nutrient medium, into the container through the liquid inlet in the upper chamber; heating or cooling the liquid medium using the means of heating or cooling to a pre-determined temperature; connecting the gas inlet in the lower chamber to a source of a compressed gas; starting the flow of the compressed gas into the lower chamber with sufficient pressure for the gas bubbles to break through the pores in the septum, enter into the upper chamber and also break the surface of the nutrient medium in the container; continuing the flow of compressed gas at a pre-determined rate of flow and for a pre-determined length of time; detecting the density and the viability of the biological culture in the nutrient medium at predetermined time intervals; detecting the concentration of the biological product in the nutrient medium at predetermined time intervals; stopping the flow of compressed gas when the viability of the biological culture or the concentration of the biological product in the nutrient medium reaches a predetermined value; adding into the upper chamber, through the liquid inlet, a sufficient quantity of a chromatography media capable of binding substantially all of the biological product and having a particle size larger than the diameter of the pores in the septum; starting the flow of compressed gas into the lower chamber to agitate the chromatography media; adjusting the pH and/or the conductivity of the nutrient medium by adding a first buffer, if needed, through the liquid inlet to cause or enhance the binding of the biological product with the chromatography media; determining the concentration of biological product in the nutrient medium until it reaches a predetermined low value; opening the liquid outlet in the bottom chamber; removing and discarding the nutrient medium and the biological culture through the liquid outlet in the lower chamber; closing the liquid outlet in the bottom chamber; adding a second buffer capable of disassociating any contaminants, bound or unbound, from the chromatography media, to the container through the liquid inlet in the upper chamber in sufficient quantity to submerge the chromatography media; starting the flow of the compressed gas to agitate the chromatography media for a predetermined length of time; opening the liquid outlet in the lower chamber to let the second buffer to flow out, and monitoring the level of contaminants and discarding the second buffer; repeating above steps, if needed, to achieve a predetermined low level of contaminants in the discarded second buffer; adding a third buffer capable of further disassociating the bound and unbound contaminants and also from 1% to 5% of the biological product, from the chromatography media, to the container through the liquid inlet in the upper chamber in sufficient quantity to submerge the chromatography media; starting the flow of gas to agitate the chromatography media for a predetermined length of time; opening the liquid outlet in the lower chamber to allow the third buffer to flow out; monitoring the concentration of the biological product in step above and discarding the third buffer removed; adding a fourth buffer capable of disassociating substantially all of the biological product from the chromatography media to the container from the liquid inlet in the upper chamber; starting the flow of gas to agitate the chromatography media for a predetermined length of time; opening the liquid outlet in the lower chamber to allow the fourth buffer to flow out; monitoring the concentration of the biological product in the step above and collecting the fourth buffer removed; repeating above steps to a predetermined low concentration of the biological product in the fourth buffer collected; combining all collected fractions of the fourth buffer.

The method for producing and purifying a biological product as described above can be used to combine the fractions and subjected to additional purification steps if necessary.

The method for producing and purifying a biological product described above would ideally have the pores in the septum that are from 1/32 inch to 1 inch apart.

The method for producing and purifying a biological product described above would ideally have the container that is substantially cylindrical, ovoid, cuboid, round, rectangular or square in shape.

The method for producing and purifying a biological product described above would ideally have the container that is generally a two-dimensional flexible bag, wherein at least the internal portion of the container is comprised of a biocompatible material.

The method for producing and purifying a biological product as described above would ideally have the container that further comprises a plurality of sensors.

The method for producing and purifying a biological product as described above can be used to grow biological culture that comprises bacteria, yeast, baculoviruses, mammalian cells or plant cells.

The method for producing and purifying biological products as described above would ideally produce the biological product is selected from the group consisting of solubilized inclusion bodies, small proteins, enamel matrix proteins, fusion proteins, tag proteins, hormones, parathyroid hormones, growth hormones, gonadotropins, insulin, ACTH, prolactin, placental lactogen, melanocyte stimulating hormone, thyrotropin, calcitonin, enkephalin, angiotensin, cytokines human serum albumin, bovine serum albumin, ovalbumin, glucose isomerase, α-amylase, endo-β-glucanase, growth hormone (GH), IGF-1, IGF-2, PTH, $PGE_2$, TGF-β, TGF-α, bEGF, EGF, PDGF-AB, PDGF-BB, osteoprotegerin (OPG), osteopontin (OP), FGF-1, FGF-2, thyroid hormone, BMP-2, BMP-3, BMP-4, BMP-6, BMP-7, VEGF, $L25(OH)_2$, vitamin $D_3$, caclitonin, IFN-alpha, IFN-beta, IFN-gamma, OCN (osteocalcin), ON (osteonectin), OP-1 (osteogenic protein-1), NGF, collagen, fibronectin, fibrinogen, thrombin, factor XIII, a recombinant protein, a recombinant antibody and a recombinant peptide.

The method for producing and purifying a biological product as described above would ideally use a chromatography media that comprises an ionic-exchange chromatography media, a hydrophobic chromatography media, an affinity chromatography media or a mixture thereof.

The method for producing and purifying a biological product as described above would ideally use the chromatography media that comprises a protein or a peptide as a ligand.

The method for producing and purifying a biological product as described above would ideally use a chromatography media that comprises a chromatography media with specific affinity towards the biological product.

The method for producing and purifying a biological product as described above may generally use a plurality of chromatography media.

The method for producing and purifying a biological product as described above would ideally have the chromatography media particles that are of a size larger than the pore diameter of the septum.

The method for producing and purifying a biological product as described above may include removing the biological product and transferring to another bioreactor and repeating the steps of purification.

The method for producing and purifying a biological product as described above, wherein the method can be used in an environment complying with ISO 7 to ISO 9 clean air standards.

COMMON EMBODIMENTS

In a first embodiment, the present invention proposes a bioreactor capable of growing all types of cells and organisms regardless of the gasifcation requirement without applying any external motion to the container and without attaching any mechanical devices to the container, either inside or outside of the bag.

In a second embodiment, the present invention proposes an additional function of a bioreactor by providing a ready means of harvesting of biological products in a bioreactor by capturing the biological product by binding it to a chromatography media. No mechanicam devices are required. Thus the present invention combines at least one significant step in the biological manufacturing of drugs with the upstream processing.

In a third embodiment, the present invention proposes a method of separating the biological product form the nutrient medium and the biological culture within the bioreactor eliminating the need for the centrifugation of the nutrient medium to remove the biological culture and filtration of the nutrient medium to reduce its volume.

In a fourth embodiment, the present invention proposes a method of purifying a biological product in a bioreactor wherein selectively binding the biological product to a chromatography media and the eluting it gradually performs the same function that is normally performed in chromatography column. Thus, in such instance, the present invention acts like a chromatography column.

In an fifth embodiment, the present invention provides a means of substantially reducing the cost of recombinant drug manufacturing by eliminating some of the most costly and time consuming steps.

In a sixth embodiment, the present invention provides a means of manufacturing hazardous biological substances without any special restrictions and also protect the biological product from environment and personnel.

PRIOR ART

The present invention is type of bubble reactor that also serves as a separative bioreactor.

The U.S. Pat. No. 7,875,448 to Furey teaches a disposable bioreactor, comprising: a container for holding a fluid culture; a first diffuser disposed within said container; an outlet tube for drawing the culture from a bottom of said container; an inlet tube for returning at least a portion of the culture from the outlet tube to said container through said diffuser, said first diffuser being disposed above said container bottom and disposed completely within the culture when said container holds the fluid culture, wherein said first diffuser disperses said returning culture to said container into a wider more distributed stream than occurs using said inlet tube without said first diffuser, wherein said first diffuser combines a gas from a source external to the container with said returning culture before said dispersion to said container. The present invention claims do not read on to this bioreactor since there is no recirculation of fluid culture (nutrient medium and biological culture mixture of the present invention); while the diffuser is described as a screen mesh in the U.S. Pat. No. 7,875,448, the present invention uses a porous septum that develops a pressure to transfer the gas into container. Additionally, the prior art merely describes a method of growing cells in a nutrient medium while the present invention uses the porous septum to act as a filter to perform several additional functions.

The U.S. Pat. No. 7,629,167 to Hodge teaches a bioreactor system comprising: a disposable container for housing biomaterials for processing, the disposable container comprising a single chamber including at least one input port; a fitting comprising a porous surface associated with the input port and configured for allowing the passage of an inlet gas stream and controlling gas bubble size and distribution prior to addition of the inlet gas stream to the interior of the single chamber, wherein the pore size of the porous surface is chosen from macro, micron, submicron, nano, and combinations thereof; a disposable mixing system comprising an impeller positioned above the porous surface and within the single chamber at a lower portion of the single chamber, the impeller configured to be driven by a motor magnetically coupled to the impeller and external to the lower portion of the single chamber such that biomaterials contained within the single chamber are mixed and gas bubble circulation is increased; at least one exhaust port; at least one harvest port; a structure for supporting the disposable container; one or more sensors for sensing one or more parameters of the biomaterials in the container; and a heater for heating the contents of the disposable container, the heater having a thermostat. This patent does not constitute a prior art for the present invention since the porous surface provided here is associated with the gas inlet and does not provide a stream that is dispersed throughout the bottom of the container as claimed in the present invention.

The U.S. Pat. No. 6,432,698 to Gaugler et al., teach a disposable bioreactor for culturing microorganisms and cells is provided. The bioreactor is suitable for use by individuals not skilled in microbiology or aseptic technique. It is constructed of flexible or semi-flexible waterproof sheets to form a container designed to provided mixing and gas exchange to microorganisms cultured therein. Mixing and gas exchanged are achieved by bubbling gas through the culture, either from a single locus at the lowermost apex of a container having a wedge-shaped or rounded bottom, or from multiple loci across a flat-bottomed container. This patent does not constitute a prior art because the present invention provides diffusion of gas from throughout the bottom of the container.

The U.S. Pat. No. 5,081,036 teaches: 1. An airlift bioreactor for growing cells which release biological products in a liquid growth medium, said bioreactor comprising: a. a growth chamber for receiving the cells and the liquid growth medium and providing an environment for cell growth, said growth chamber having internal side walls which define a middle region; b. means for gently bubbling a stream of gas up through the middle region of said growth chamber to thereby cause gentle circulation of the liquid growth medium up through the middle region of said growth chamber and then back down along the internal side wall of said growth chamber; and c. stainless steel filament sponge located within said growth chamber to intersect at least a portion of gentle circulation of liquid growth medium present in said bioreactor when said bioreactor is in operation, said stainless steel sponge having a surface area and filament spacing sufficient to facilitate absorption of at least a portion of the gas stream into the liquid growth medium and to entrap or attach the cells within the sponge, yet maintain gentle circulation of the liquid medium. This reference for an airlift bioreactor does not constitute a prior art for the present invention.

A search of the US patent database for bubble reactors providing a "preparative" function yielded one reference. The U.S. Pat. No. 6,723,555 to Downs teaches a fermentation apparatus is constructed to produce a known and repeatable amount of untainted fermentation product using multiple fermentation vessels. To facilitate further processing compatible with other product processing steps, the fermentation apparatus has an array of sample vessels arranged in a container frame. The container frame is configured to hold the sample vessels during fermentation and to transport the vessel array to or from another processing station. Corresponding to the number of sample vessels in the sample vessel array, a cannula array is configured such that each cannula may be placed inside a sample vessel. The cannula array is attached to a gas distributor that delivers oxygen and/or one or more other gases from a gas source through the cannula into the sample vessel. Because the fermentation volume for each individual sample vessel is smaller than a bulk fermentation apparatus, the fermentation product yields are predictable and cell growth rates can be effectively optimized. This reference does not constitute a prior art for the present invention.

The U.S. Pat. No. 7,699,976 to Hansen et al teaches an upflow bioreactor that includes a vessel having an inlet and an outlet configured for upflow operation. A septum is positioned within the vessel and defines a lower chamber and an upper chamber. The septum includes an aperture that provides fluid communication between the upper chamber and lower chamber. The bioreactor also includes means for releasing pressure buildup in the lower chamber. In one configuration, the septum includes a releasable portion having an open position and a closed position. The releasable portion is configured to move to the open position in response to pressure buildup in the lower chamber. In the open position fluid communication between the lower chamber and the upper chamber is increased. Alternatively the lower chamber can include a pressure release line that is selectively actuated by pressure buildup. The pressure release mechanism can prevent the bioreactor from plugging and/or prevent catastrophic damage to the bioreactor caused by high pressures. This reference does not constitute a prior art for the present invention as the septum provided in the present invention is not breached during the use.

A search of the US patent database for bubble reactors providing a "separative" function yielded no reference.

Argonne scientists (www.anl.gov) recently used electrical force to transport organic acids away from the biocatalyst across an ion-exchange membrane and into a concentrate chamber, very similar to normal metabolism processes for handling acids. To provide the electricity in a cost efficient fashion, researchers turned to electrodeionization (EDI). EDI is an established commercial technology for producing high-purity water. Previously, Argonne scientists modified EDI so that it could be used for desalination of chemical and agricultural products. To accomplish this, researchers molded loose ion exchange chromatography media beads into a porous chromatography media wafer, enabling the capture of charge salts and acids at dilution levels with high-energy efficiency and significantly reduced waste streams compared to conventional processing. This became the basis for the Argonne's separative bioreactor. Researchers also realized that although direct enzyme immobilization on membranes provided excellent product separations, insufficient enzyme density limited the overall performance. In order to increase the density, the scientists integrated enzyme immobilization technology into the porous chromatography media wafer and created a material that can efficiently produce and remove organic acids. As Argonne designed its separative bioreactor, researchers incorporated enzyme capture chromatography media beads into the chromatography media wafer. Sugars were converted by the immobilized biocatalyst to the target acids, and the product was electrically transported into a concentrate channel. This resulted in reactions occurring without buffering or neutralization. Argonne's immobilization technology also allows in-situ stripping and replacement of degraded enzymes without disassembling the system. The inventions of Argonne for a separative bioreactor are described in U.S. Pat. No. 6,797,140 (Electrodeionization method, U.S. Pat. No. 6,495,014 (Electrodeionization substrate, and device for electrodeionization treatment), Ser. No. 24/060,875A1 (Electrodeionization method), Ser. No. 24/115,783A1 (Immobilized biocatalytic enzymes in electrodeionization), Ser. No. 25/056,547A1 (Single stage separation and esterification of cation salt carboxylates using electrodeionization). None of these references form a prior art for the present invention.

The US patents that describe a separative bioreactor include: U.S. Pat. No. 8,007,647 Retention of counterions in the separative bioreactor; U.S. Pat. No. 7,981,261 Integrated device and substrate for separating charged carriers and reducing photocorrosion and method for the photoelectrochemical production of electricity and photocatalytic production of hydrogen; U.S. Pat. No. 7,141,154 Single-stage separation and esterification of cation salt carboxylates using electrodeionization. None of these patents constitute a prior art for the present invention.

The U.S. Pat. Nos. 7,977,395 Electronically and ionically conductive porous material and method for manufacture of resin wafers therefrom; 7,799,548 Method of stripping genetically tagged biomolecules from porous solid ion exchange wafer; 7,507,318 Devices using resin wafers and applications thereof; 7,452,920 Electronically and ionically conductive porous material and method for manufacture of resin wafers therefrom; and 7,306,934 Porous solid ion exchange wafer for immobilizing biomolecules teach a porous solid ion exchange wafer comprising a combination of an biomolecule: capture-chromatography media and an ion-exchange chromatography media forming a charged capture chromatography media containing a transition metal anion of +2 valence within said wafer. Additionally, this application claims a separative bioreactor, comprising an anode and a cathode, a plurality of reaction chambers at least some being formed from a porous solid ion exchange wafers having a combination of an biomolecule capture-chromatography media and an ion-exchange chromatography media forming a charged capture chromatography media within said wafer and having a genetically tagged biomolecule immobilized on said charged capture chromatography media, each of said porous solid ion exchange wafers having a charged capture chromatography media therewithin being interleaved between a cation exchange membrane and an anion exchange membrane, and mechanism for supplying an electric potential between the anode and the cathode. None of these disclosures are common to the present invention and the essential features of the present invention are not recited in the present invention.

In summary, there is no prior art in the literature on which the claims made in the present invention could be read on. Using a flexible porous septum to introduce gas and mix liquids and using chromatography media to harvest and purify a biological product is novel, unobvious and useful.

I claim:

1. A method for producing and purifying a biological product in an uncontrolled environment comprising:
   providing a disposable container for housing a nutrient media, the disposable container comprising an upper chamber and a lower chamber separated by a porous flexible membrane with a plurality of pores ranging from 10 microns to 1000 microns, at least one gas inlet port in the lower chamber, at least one liquid outlet port in the lower chamber, at least one gas exhaust port in the upper chamber, at least one liquid inlet port in the upper chamber, a structure for supporting the disposable container, one or more sensors for sensing one or more parameters of the nutrient media in the disposable container, and a heater for heating the contents of the disposable container, the heater having a thermostat;
   adding to the disposable container the nutrient media and a biological culture capable of secreting the biological product, through the liquid inlet in the upper chamber;
   starting and continuing supplying a gas through the gas inlet in the lower chamber of the disposable container to mix the nutrient media and the biological culture and to achieve and maintain a pre-determined level of gas concentration in the nutrient media;
   adding a sufficient quantity of a chromatography media having a particle size larger than the diameter of the pores in the porous flexible membrane through the liquid inlet in the upper chamber when a pre-determined level of the biological product has reached in the nutrient media to bind essentially all of the biological product in the nutrient media;

removing and discarding the nutrient medium and the biological culture through the liquid outlet in the lower chamber;

adding at least once a buffer suitable for disassociating the biological product from the chromatography media in the disposable container through the liquid inlet in the upper chamber;

removing the buffer through the liquid outlet as a concentrated purified solution of the biological product.

2. The method for producing and purifying a biological product in an uncontrolled environment according to claim 1, wherein the biological culture comprises bacteria, yeast, baculovirus, mammalian cells or plant cells.

3. The method for producing and purifying a biological product in an uncontrolled environment according to claim 1, wherein the chromatography media comprises an ionic-exchange chromatography media, a hydrophobic chromatography media, an affinity chromatography media, a peptide, a protein or a mixture thereof.

4. The method for producing and purifying a biological product in an uncontrolled environment according to claim 1 where the environment complies with ISO class of air 14644 standards.

* * * * *